United States Patent [19]  [11] Patent Number: 4,983,398
Gaylord et al. [45] Date of Patent: Jan. 8, 1991

[54] SUSTAINED RELEASE DRUG DOSAGE FORMS CONTAINING HYDROXYPROPYLMETHYLCELLULOSE AND ALKALI METAL CARBOXYLATES

[75] Inventors: Norman G. Gaylord, New Providence, N.J.; Ashok Nigalaye, East Rockaway, N.Y.

[73] Assignee: Forest Laboratories, Inc., New York, N.Y.

[21] Appl. No.: 284,931

[22] Filed: Dec. 15, 1988

Related U.S. Application Data

[63] Continuation-in-part of Ser. No. 135,667, Dec. 21, 1987, abandoned.

[51] Int. Cl.$^5$ ................................................ A61K 9/20
[52] U.S. Cl. .................................... 424/465; 424/433; 424/434; 424/435; 424/436; 424/464
[58] Field of Search ............... 424/494, 464, 465, 433, 424/434, 435, 436

[56] References Cited

U.S. PATENT DOCUMENTS

| | | | |
|---|---|---|---|
| 3,065,143 | 11/1962 | Christenson et al. | 167/82 |
| 3,590,117 | 6/1971 | Christenson et al. | 424/19 |
| 3,870,790 | 3/1975 | Lowey et al. | 424/19 |
| 4,126,672 | 11/1978 | Sheth et al. | 424/22 |
| 4,140,755 | 2/1979 | Sheth et al. | 424/21 |
| 4,167,558 | 9/1979 | Sheth et al. | 424/22 |
| 4,226,849 | 10/1980 | Schor | 424/19 |
| 4,259,314 | 3/1981 | Lowey | 424/19 |
| 4,369,172 | 1/1983 | Schor et al. | 424/19 |
| 4,389,393 | 6/1983 | Schor et al. | 424/19 |
| 4,540,566 | 9/1985 | Davis et al. | 424/22 |
| 4,666,705 | 5/1987 | DeCrosta et al. | 424/482 |

FOREIGN PATENT DOCUMENTS 2176999 1/1987 United Kingdom .

OTHER PUBLICATIONS

L. C. Feely et al., "Influence of Surfactants on Drug Release from Hydroxypropyl Methyl Cellulose Matrices", *Chemical Abstracts*, 108, p. 437 (1988).
L. C. Feely et al., "Influence of Surfactants on Drug Release from Hydroxypropyl Methyl Cellulose Matrices", *Int. J. Pharm.*, 41, pp. 83-90 (1988).
H. Lapidus and N. G. Lordi, "Some Factors Affecting the Release of a Water-Soluble Drug from a Compressed Hydrophilic Matrix", J. Pharm. Sci., 55 (8), 840-843 (1966).
H. E. Huber, L. B. Dale and G. L. Christenson, "Utilization of Hydrophilic Gums for the Control of Drug Release from Tablet Formulations, I, Disintegration and Dissolution Rehavior", J. Pharm. Sci., 55 (9), 974-976 (1966).
H. Lapidus, "Drug Release from Compressed Hydrophilic Matrices", Ph.D. Thesis, Rutgers University, New Jersey, May 1967.
H. Lapidus and N. G. Lordi, "Drug Release from Compressed Hydrophilic Matrices", J. Pharm. Sci., 57 (8), 1292-1301 (1968).
J. A. Salomon, E. Doelker and P. Buri, "Importance de la Technologie et de la Formulation pour le Mecanisme de Liberation du Chlorure de Potassium Contenu dans des Matrices Hydrophiles", Pharm. Acta Helv., 54 (3), 82-85 (1979).
P. D. Daly, S. S. Davis and J. W. Kennerley, "The Effect of Anionic Surfactants on the Release of Chlorpheniramine from a Polymer Matrix Tablet", Inter. J. Pharm., 18, 201-205 (1984).

*Primary Examiner*—Thurman K. Page
*Attorney, Agent, or Firm*—Ricahrd M. Barnes; John J. Cassingham

[57] ABSTRACT

A therapeutically active solid unit dosage form comprising a carrier base material combined with a therapeutically active medicament and shaped and compressed to a solid unit dosage form having a controlled and sustained release pattern upon administration, the carrier base material comprising a mixture of one or more nonionic cellulose ethers and an alkali metal carboxylate, wherein at least one of the cellulose ethers is hydroxypropylmethylcellulose having a number average molecular weight of at least 50,000.

10 Claims, No Drawings

SUSTAINED RELEASE DRUG DOSAGE FORMS CONTAINING HYDROXYPROPYLMETHYLCELLULOSE AND ALKALI METAL CARBOXYLATES

CROSS REFERENCE TO RELATED APPLICATION

This application is a continuation-in-part application of U.S. patent application Ser. No. 135,667, filed Dec. 21, 1987 now abandoned.

BACKGROUND OF THE INVENTION

This invention relates to a carrier base material that is combined with a therapeutically active medicament and formed into a solid, shaped unit dosage form having a controlled and sustained incremental release of the medicament upon administration. The carrier base material of this invention comprises a mixture of a water-soluble hydroxypropylmethylcellulose and an alkali metal carboxylate, which carrier base desirably may be present in an amount less than 30 weight-% of the dosage form thereby permitting the administration of high dosage medicaments.

The administration of a medicament which requires a high dosage for effective therapy mandates a single, potentially toxic, dose or multiple doses. Alternatively, controlled and sustained release of a medicament from a solid unit dosage form provides for continuous dosage from a single administration. However, in order to accommodate a sufficient amount of a high dosage medicament in a solid unit dosage form, without significantly increasing the size of the latter, it is necessary to utilize a carrier base material which is effective, at low concentrations, in retarding the release of the medicament.

Hydroxypropylmethylcelluloses have been widely used as binders, matrices or carrier bases in sustained release solid dosage forms containing active medicaments, accompanied by lubricants and excipients, as needed. Commercially available hydroxypropylmethylcellulose is actually a series of compounds, each of which has a different chemical structure and composition, with a methoxyl content within the range of 16.5 to 30 weight-% and a hydroxypropoxyl content within the range of 4 to 32 weight-%, and each of which is available in various viscosity grades.

Commercial designations of the various hydroxypropylmethylcelluloses are based on the viscosities of 2% aqueous solutions at 20° C. The viscosities range from 5 to 100,000 cps (mPa.sec) and represent number average molecular weights ranging from below 10,000 to over 150,000, as calculated from the data in "Handbook of Methocel Cellulose Ether Products" (The Dow Chemical Co., 1974).

Christenson and Dale (U.S. Pat. No. 3,065,143) and Huber, Dale and Christenson (J. Pharm. Sci., 55, 974 (1966)) disclosed the preparation of a sustained release drug tablet wherein a high viscosity grade, i.e. high molecular weight, hydroxypropylmethylcellulose, was present as binder to the extent of at least one third of the weight of the tablet. The binders included a 4000 mPa.sec viscosity grade hydroxypropylmethylcellulose, now known as Methocel E4M, having a 28-30 weight-% methoxyl content, a 7.5-12 weight-% hydroxypropoxyl content and a number average molecular weight of 93,000, as well as 4000 and 15,000 mPa.sec viscosity grades hydroxypropylmethylcelluloses, now known as Methocel K4M and K15M, respectively, having a 19-24 weight-% methoxyl content, a 4-12 weight-% hydroxypropoxyl content and number average molecular weights of 89,000 and 124,000, respectively.

Christenson and his coworkers proposed that water was rapidly absorbed and formed a gel barrier on the surface of the tablet. Drug release was controlled by drug diffusion from and attrition of the gel barrier.

Christenson and Huber (U.S. Pat. No. 3,590,117) reported that neither low nor high viscosity grade hydroxypropylmethylcelluloses made acceptable longlasting troches.

Lapidus (Dissertation, Rutgers State University, 1967) and Lapidus and Lordi (J. Pharm. Sci., 55, 840 (1966); 57, 1292 (1968)) reported on the use of 25 and 15,000 mPa.sec viscosity grades hydroxypropylmethylcelluloses having a 19-24 weight-% methoxyl content and 4-12 weight-% hydroxypropoxyl content, i.e., Methocel K25 and K15M, respectively, in compressed pharmaceutical tablets.

Salomon, Doelker and Buri (Pharm. Acta Helv., 54 (3), 82 (1979)) disclosed the need for more than 30 weight-% of a 15,000 mPa.sec viscosity grade hydroxypropylmethylcellulose with 19-24 weight-% methoxyl content and 4-12 weight-% hydroxypropoxyl content (Methocel K15M) in a tablet containing potassium chloride, in order to sustain the release of drug for more than a few hours.

Sheth and Tossounian (U.S. Pat. Nos. 4,126,672; 4,140,755; 4,167,558) disclosed solid dosage forms containing 20-75% of a hydrocolloid such as 4000 mPa.sec viscosity grade hydroxypropylmethylcellulose in combination with various additives including gas-generating compounds, e.g. calcium carbonate, and inert fatty materials, resulting in a hydrodynamically balanced product having a bulk density of less than one when it is in contact with gastric fluid and hence floating on and releasing medicament therein.

Schor, Nigalaye and Gaylord (U.S. Pat. No. 4,389,393) disclosed sustained release solid unit dosage forms in which the carrier base material constituted less than one third of the weight of the dosage form and consisted of hydroxypropylmethylcellulose of at least 4000 mPa.sec viscosity grade, representing a number average molecular weight of at least 50,000, and having a methoxyl content of 16-24 weight-% and a hydroxypropoxyl content of 4-32 weight-%, e.g., Methocel J and Methocel K.

The use of high viscosity grades of hydroxypropylmethylcelluloses, Methocel E, F and K, in sustained release solid drug dosage forms is also described in a technical bulletin "Formulating Sustained Release Pharmaceutical Products with Methocel" (The Dow Chemical Co., 1982).

The prior art cited hereinabove discloses that high viscosity grades of hydroxypropylmethylcellulose of various chemical compositions are useful in the preparation of sustained release solid drug dosage forms. In contrast, Schor, Nigalaye and Gaylord (U.S. Pat. No. 4,369,172) disclosed that sustained release therapeutic compositions could be prepared by using as a carrier base material, a low viscosity grade hydroxypropylmethylcellulose having a hydroxypropoxyl content of 9-12 weight-% and a number average molecular weight of less than 50,000.

Lowey and Stafford (U.S. Pat. No. 3,870,790) and Schor (U.S. Pat. No. 4,226,849) disclosed that effective sustained release tablets were produced by using as carrier base material, a modified low viscosity grade hydroxypropylmethylcellulose having a hydroxypropoxyl content of less than 9 weight-% and a number average molecular weight of 23,000, e.g., Methocel E50. The modification was carried out by exposure of the low molecular weight hydroxypropylmethylcellulose to high humidity or moisture and drying in air, resulting in an increase in the carboxyl content of the polymer.

Davis and Gaylord (U.S. Pat. No. 4,540,566) and Daly, Davis and Kennerley (International J. Pharmaceutics, 18, 201 (1984)) disclosed that the presence of an alkali metal sulfate or sulfonate prolonged the release pattern of a medicament from a tablet containing the modified low viscosity grade hydroxypropylmethylcellulose as carrier base material.

Lowey (U.S. Pat. No. 4,259,314) disclosed the use of a mixture of dried hydroxypropylmethylcellulose having a viscosity in the range of 50 to 4000 mPa.sec, and hydroxypropylcellulose in the preparation of a controlled release pharmaceutical composition.

The present invention relates to further improvements in carrier base materials containing high molecular weight hydroxypropylmethylcelulose and high dosage prolonged release solid pharmaceutical unit dosage forms containing such improved carrier base materials. These improvements result from the presence of an alkali metal carboxylate in the carrier base material.

SUMMARY OF THE INVENTION

An object of the present invention is to provide a therapeutically active solid unit dosage form having a controlled and prolonged release pattern comprising a carrier base material in combination with a therapeutically active medicament. The composition of the invention may be administered orally, buccally, sublingually, etc., in the form of lozenges and tablets, as well as suppositories and other solid unit dosage forms.

Another object of the present invention is to provide a sustained release therapeutically active solid unit dosage form having improved sustained release characteristics.

A further object of the present invention is to provide an improved carrier base material for use in high dosage solid pharmaceutical unit dosage forms.

Yet other objects of the present invention are to provide methods for making such therapeutically active solid unit dosage forms and carrier bases for such dosage forms.

In one embodiment, the present invention is directed to a therapeutically active solid unit dosage form having a controlled and sustained release pattern upon administration comprising a mixture of a therapeutically active medicament and a carrier base material comprising (a) one or more water-soluble nonionic cellulose ethers, wherein at least one of the cellulose ethers is a hydroxypropylmethycellulose having a number average molecular weight of at least 50,000, and (b) an alkali metal carboxylate, wherein the carrier base comprises less than 30 weight-% of the total weight of the dosage form.

In a second embodiment, the therapeutically active solid unit dosage form of the invention comprises a mixture of a therapeutically active medicament and a carrier base material that consists essentially of (a) one or more water-soluble nonionic cellulose ethers, wherein at least one of the cellulose ethers is a hydroxypropylmethylcellulose having a number average molecular weight of at least 50,000, and (b) an alkali metal carboxylate.

Preferably, the ratio of cellulose ether to alkali metal carboxylate in the carrier base ranges from 1/0.05 to 1/3. The hydroxypropylmethylcellulose content of the composition preferably constitutes from 3 to 25 weight-% of the dosage form, with the therapeutically active medicament preferably constituting at least 70 weight-% of the dosage form.

Particularly preferred hydroxypropylmethylcellulose materials for use in the carrier base are materials that (a) have a methoxyl content of 28–30 weight-% and a hydroxypropoxyl content of 7.5–12 weight-%, and (b) have a methoxyl content of 19–24 weight-% and a hydroxypropoxyl content of 4–12 weight-%.

The akali metal carboxylate that is used in the composition preferably is a salt of a $C_8$ to $C_{40}$ carboxylic acid. Most preferably, sodium stearate or sodium laurate is used.

The carrier base materials and therapeutically active medicament may be homogeneously mixed together by any suitable mixing technique. To obtain a solid unit dosage form, suitable quantities of the ingredients are mixed, shaped and compressed under conditions to yield a solid unit dosage form having the desired size and sustained release characteristics.

DETAILED DESCRIPTION OF THE INVENTION

According to the present invention, it has now been found that important advantages and improvements over prior art products containing water-soluble nonionic cellulose ethers, particularly high molecular weight hydroxypropylmethylcelluloses, as carrier base materials, can be obtained by admixture of the hydroxypropylmethylcellulose with an alkali metal carboxylate.

The hydroxypropylmethylcelluloses that are effective in the present invention include, but are not limited to, commercially available high viscosity grades, i.e., high molecular weight hydroxypropylmethylcelluloses. These include all grades having a number average molecular weight of at least 50,000, independent of chemical structure. Thus, hydroxypropylmethylcelluloses having the following methoxyl and hydroxypropoxyl contents are effective when the viscosity grade is at least about 500 mPa.sec:

| Methocel | Methoxyl content weight % | Hydroxypropoxyl content weight % |
|---|---|---|
| E | 28–30 | 7.5–12 |
| F | 27–30 | 4.0–7.5 |
| J | 16.5–20 | 23–32 |
| K | 19–24 | 4–12 |

The use of low concentrations of high viscosity grades of hydroxypropylmethylcellulose as the carrier base material in a solid unit dosage form has been disclosed in U.S. Pat. No. 4,389,393. It has now surprisingly been found that the presence of an alkali metal carboxylate results in an even more prolonged and sustained release time than is obtainable with the use of the hydroxypropylmethylcellulose at the same concentration in the dosage form in the absence of the alkali metal carboxylate. This permits the preparation of unit dosage forms having a higher concentration of active medicament, while at the same time maintaining the desired prolonged and sustained release characteristics.

The alkali metal carboxylates that are effective in the present invention include alkali metal salts of $C_8$ to $C_{40}$ carboxylic acids. The acids may have a branched or straight hydrocarbon chain structure, may contain alicyclic and/or aromatic moieties and may be saturated or unsaturated. Representative alkali metal carboxylates include sodium caprylate, sodium pelargonate, sodium laurate, potassium palmitate, sodium stearate, sodium arachidate, sodium behenate, potassium lignocerate, sodium oleate, potassium oleate, sodium ricinoleate, sodium linoleate and the like.

The weight ratio of hydroxypropylmethylcellulose to alkali metal carboxylate in the solid dosage forms desirably is from 1/0.05 to 1/3 and their combined weight preferably is no more than 30 weight-% of the total weight of the solid dosage form. The solid dosage forms may desirably contain from 3 to 25 weight-% of the hydroxypropylmethylcellulose. Preferably, the therapeutically active medicament comprises at least 70 weight-% of the total weight of the dosage form.

Although the exact nature of the interaction between the akali metal carboxylate and the hydroxypropylmethycellulose is not known and we do not wish to be bound to any theory, it is believed that the admixture of those two components results in an ion-dipole interaction. When the solid unit dosage form is placed in an aqueous medium, the hydrocarbon moiety in the bonded alkali metal carboxylate promotes hydrophobic bonding between hydroxypropylmethylcellulose chains, thus retarding the release of medicament incorporated therein to an even greater extent than from the swollen hydroxypropylmethylcellulose alone.

The hydroxypropylmethylcellulose of the present invention may be used with or without prior humidification or similar treatment and when mixed with the alkali metal carboxylate and an active medicament, the mixture has excellent compressibility. The tablets prepared therefrom are hard and dense, have low friability and provide controlled and sustained release over an extended period. Solid drug forms of the present invention are stable and their release rate does not change to any significant (if any) extent over an extended period of storage.

A hydroxypropylmethylcellulose having a number average molecular weight of at least 50,000 may be used as the sole cellulose ether, in admixture with an alkali metal carboxylate, in the carrier base material or may be used in admixture with other nonionic cellulose ethers. Preferably, the hydroxypropylmethylcellulose having a number average molecular weight of at least 50,000 constitutes at least 3 weight-% of the total weight of the solid dosage form.

The active ingredient can be of any type of medication which acts locally in the mouth or systemically. Unit dosage forms that contain a systemic medicament can be administered orally to transmit the active medicament into the gastrointestinal tract and into the blood, fluids and tissues of the body without excessive peak concentrations occurring. Alternatively, the active medicament can be of any type of medication which acts through the buccal tissues of the mouth to transmit the active ingredient directly into the blood stream, thus avoiding first pass liver metabolism and bypassing the gastric and intestinal fluids which have an adverse inactivating or destructive action on many active ingredients unless they are especially protected against such fluids (e.g., by means of an enteric coating or the like). The active medicament can also be of a type of medication which can be transmitted into the blood circulation through the rectal tissues. Thus, the invention is applicable to sublingual lozenges, buccal tablets, suppositories and compressed tablets. The latter are intended to be swallowed in unit dosage form and upon ingestion according to a prescribed regimen give controlled and slow release of the active medicament, while being protected against inactivating gastric fluids.

Representative active medicaments include antacids, antiinflamatory substances, coronary vasodilators, cerebral vasodilators, peripheral vasodilators, antiinfectives, psychotropics, antimanics, stimulants, antihistamines, laxatives, decongestants, vitamins, gastrointestinal sedatives, antidiarrheal preparations, antianginal drugs, antiarrythmics, antihypertensive drugs, vasoconstrictors and migraine treatments, anticoagulants and antithrombotic drugs, analgesics, antipyretics, hypnotics, sedatives, antiemetics, antinauseants, anticonvulsants, neuromuscular drugs, hyper and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs, and other drugs or substances acting locally in the mouth, such as topical analgesics, local anaesthetics, etc.

The mixture of alkali metal carboxylate and hydroxypropylmethylcellulose having a number average molecular weight of at least 50,000, forms what is called a long-acting, slow dissolving carrier of such a nature that iL has a protective, demuloent and buffering effect in the body and causes the active medicament to exert its optimum therapeutic action immediately and incrementally for an extended period of time, so that full therapeutic advantage can be taken of the entire or substantially the entire amount of active medicament administered. This unexpectedly high degree of efficiency is a particular advantage of the invention nd minimizes the side effects of the medication.

In preparing tablets containing an orally administrable systemically absorbable active component such as one of the heretofore mentioned medicaments, the hydroxypropylmethylcellulose and the alkali metal carboxylate are thoroughly intermixed with the medicament, which is in powdered or granular form or in solution, and any other needed ingredients which are conventional in tablet making such as magnesium stearate, stearic acid, lactose, starch, fumed silica, hydrogenated vegetable oil and, in general, binders, fillers, disintegrating agents and the like. The hydroxypropylmethylcellulose and the alkali metal carboxylate may be mixed in water, alcohol or other media known in the art, and dried to produce granules before intermixing with the medicament and other ingredients. Alternatively, the medicament may be granulated with the hydroxypropylmethylcellulose and the alkali metal carboxylate before intermixing with the other ingredients.

The complete mixture, in an amount sufficient to make a uniform batch of tablets, e.g. 50,000, of which each contains an effective amount of active medicament, is then subjected to tabletting in conventional tabletting machines at compression pressures of $135 \times 10^5$ to $1100 \times 10^5$ Pa and, because of the use of the specific carrier material of this invention in the production of the tablets, a product is obtained which has the desired hardness, low level of friability and a predetermined controlled and sustained action and a regular delayed release pattern so that the medicament is available over a period of 0.25-36 hours, depending upon the precise tablet size, hardness and the particular carrier composition. In this way, it is possible to produce controlled and slow continuous release tablets in a relatively simple and economical manner on a commercial scale, in contrast with more elaborate and more complex materials and procedures heretofore employed or proposed.

The moisture content of the carrier used in the preparation of the controlled release tablets may be in the 0.1-10% range, the lower end of the range being preferable when moisture sensitive medicaments are used. If the moisture content is outside of this range, it may be brought within the range by the use of ambient or hot, dry or wet air, using appropriate equipment including static, convection, forced air or vacuum chambers or other equipment well known to those skilled in the art. The moisture content of the carrier during tabletting influences the integrity of the tablet obtained under a given compression pressure. However, the moisture content has less influence on the controlled release characteristics than the composition of the carrier and its concentration The release pattern of active medicament from the carrier of the present invention can be controlled according to the particular medication and its intended therapeutic effect. For a sublingual lozenge or tablet, the release pattern may be varied from 0.25 to 4 hours. For buccal tablets, the release period may be 0.25 to 24 hours. For orally administered tablets, the release time may be 2-4 hours, 4-8 hours, 8-10 hours 15-18 hours 20-24 hours, etc., as desired. For vaginal and rectal suppositories, the release pattern ranges from 2 to 36 hours and can be more or less where indicated. Predetermined release patterns of unusually reliable characteristics can be secured. The invention is of very versatile and adaptable nature, giving it a wide range of application and end use.

The following illustrative embodiments of the disclosures of the present invention are non-limiting and variations will be obvious to those skilled in the art.

EXAMPLES 1-2

Controlled release theophylline tablets were prepared from granular, anhydrous theophylline and 4000 mPa.sec viscosity grade hydroxypropyl methylcellulose (HPMC) having 19-24 weight-% methoxyl content, 4-12 weight-% hydroxypropoxyl content and a number average molecular weight of 89,000, commercially available as Methocel K4M. The tablets were prepared in the absence and in the presence of sodium stearate.

The 306 mg theophylline tablets were prepared from the following ingredients:

| | Example No. | |
|---|---|---|
| | 1 | 2 |
| Ingredients | mg/ tablet | mg/ tablet |
| 1. Theophylline, anhydrous | 306 | 306 |
| 2. HMPC K4M | 36 | 36 |
| 3. Sodium stearate | 0 | 36 |
| 4. Fumed silica | 1.5 | 1.5 |
| 5. Stearic acid | 3.5 | 3.5 |

Ingredients 1 and 2 were mixed, ingredient 3 was added to the blend and, after mixing, was followed by ingredients 4 and 5. The mixture was blended for 20 minutes and then subjected to compression in a Parr pellet press using a 9.525 mm die. The hardness of the tablets was determined on a Pennwalt Stokes hardness tester.

The release rates were determined at pH 1.5 using the rotating basket dissolution apparatus described in U.S. Pharmacopeia, volume XX, page 959. The basket was rotated at a speed of 100 rpm and the aqueous medium was maintained at 37° C. The results are tabulated below:

| | Example No. | | | |
|---|---|---|---|---|
| | 1 | | 2 | |
| Sodium stearate | Absent | | Present | |
| Weight, mg | 347 | | 383 | |
| Thickness, mm | 4.00 | | 4.00 | |
| Hardness, kg | 4.0 | | 4.0 | |
| Release rate Hour | % | Cumulative % | % | Cumulative % |
| 1 | 50.0 | 50.0 | 27.0 | 27.0 |
| 2 | 12.1 | 62.1 | 9.6 | 36.6 |
| 3 | 12.9 | 75.0 | 11.5 | 48.1 |
| 4 | 9.7 | 84.7 | 7.0 | 55.1 |
| 5 | 8.6 | 93.3 | 6.9 | 62.0 |
| 6 | 8.6 | 101.9 | 6.4 | 68.4 |
| 7 | — | — | 5.8 | 74.2 |

The release rates were also determined at pH 7.0 using the rotating paddle dissolution apparatus described in the U.S. Pharmacopeia, volume XX, page 959. The paddle was rotated at a speed of 50 rpm and the aqueous medium was maintained at 37° C., with the following results:

| | Example No. | | | |
|---|---|---|---|---|
| | 1 | | 2 | |
| Sodium stearate | Absent | | Present | |
| Release rate Hour | % | Cumulative % | % | Cumulative % |
| 1 | 33.2 | 33.2 | 15.4 | 15.4 |
| 2 | 14.1 | 47.3 | 7.9 | 23.3 |
| 3 | 10.3 | 57.6 | 6.2 | 29.5 |
| 4 | 8.1 | 65.7 | 4.6 | 34.1 |
| 5 | 6.7 | 72.4 | 4.0 | 38.1 |
| 6 | 5.1 | 77.5 | 3.7 | 41.8 |
| 7 | 4.3 | 81.8 | 3.3 | 45.1 |
| 8 | 2.8 | 84.6 | 3.2 | 48.3 |
| 9 | 2.2 | 86.8 | 3.2 | 51.5 |
| 10 | 1.3 | 88.1 | 3.1 | 54.6 |
| 12 | 0.9 | 89.0 | 5.4 | 60.0 |
| 14 | 0.3 | 89.3 | 5.0 | 65.0 |
| 16 | 0.3 | 89.6 | 4.4 | 69.4 |
| 18 | 0.4 | 90.0 | 4.0 | 73.4 |

EXAMPLES 3-4

Controlled release theophylline tablets were prepared from anhydrous theophylline and 4000 mPa.sec viscosity grade hydroxypropylmethylcellulose (HPMC) having 28-30 weight-% methoxyl content, 7.5-12 weight-% hydroxypropoxyl content and a number average molecular weight of 93,000, commercially available as Methocel E4M. The tablets were prepared in the absence and in the presence of sodium laurate.

The 306 mg theophylline tablets were prepared from the following ingredients:

|  | Example No. | |
|---|---|---|
|  | 3 | 4 |
| Ingredients | mg/tablet | mg/tablet |
| 1. Theophylline, anhydrous | 306 | 306 |
| 2. HPMC E4M | 36 | 36 |
| 3. Sodium laurate | 0 | 36 |
| 4. Fumed silica | 1.5 | 1.5 |
| 5. Stearic acid | 3.5 | 3.5 |

The ingredients were mixed in the same manner as in Examples 1–2 and compressed in a pellet press using a 9.525 mm die.

The release rates were determined at pH 1.5 at 37° C. using the rotating basket method at 100 rpm. The 306 mg theophylline tablets had the following properties:

|  | Example No. | | | |
|---|---|---|---|---|
|  | 3 | | 4 | |
| Sodium laurate | Absent | | Present | |
| Weight, mg | 347 | | 383 | |
| Thickness, mm | 3.80 | | 4.50 | |
| Hardness, kg | 4.0 | | 4.0 | |
| Release rate | | Cumulative | | Cumulative |
| Hour | % | % | % | % |
| 1 | 32.3 | 32.3 | 29.4 | 29.4 |
| 2 | 14.8 | 47.1 | 12.1 | 41.5 |
| 3 | 14.3 | 61.4 | 9.5 | 51.0 |
| 4 | 15.3 | 77.7 | 11.3 | 62.3 |
| 5 | 11.6 | 89.3 | 9.1 | 71.4 |
| 6 | 2.2 | 91.5 | 8.3 | 79.7 |
| 7 | 3.9 | 95.4 | 8.0 | 87.7 |

The release rates were also determined at pH 7.0 at 37° C. using the rotating paddle method at 50 rpm., with the following results:

|  | Example No. | | | |
|---|---|---|---|---|
|  | 3 | | 4 | |
| Sodium laurate | Absent | | Present | |
| Release rate | | Cumulative | | Cumulative |
| Hour | % | % | % | % |
| 1 | 33.5 | 33.5 | 24.6 | 24.6 |
| 2 | 14.2 | 47.7 | 11.0 | 35.6 |
| 3 | 10.5 | 58.2 | 7.9 | 43.5 |
| 4 | 8.1 | 66.3 | 7.2 | 50.7 |
| 5 | 7.6 | 73.9 | 7.0 | 57.7 |
| 6 | 6.8 | 80.7 | 7.6 | 65.3 |
| 7 | 6.0 | 86.7 | 7.5 | 72.8 |
| 8 | 4.9 | 91.6 | 7.2 | 80.0 |
| 9 | 3.8 | 95.4 | 6.4 | 86.4 |
| 10 | 2.4 | 97.8 | 5.1 | 91.5 |
| 12 | 0.9 | 99.7 | 6.6 | 98.1 |
| 14 | 0.7 | 100.4 | 3.3 | 101.4 |

EXAMPLE 5

Controlled release theophylline tablets were prepared from anhydrous theophylline and the 4000 mPa.sec viscosity grade HPMC (Methocel E4M) used in EXAMPLES 3–4, in the presence of sodium stearate.

The 3–6 mg theophylline tablets were prepared from the following ingredients:

| Ingredients | mg/tablet |
|---|---|
| 1. Theophylline, anhydrous | 306 |
| 2. HPMC E4M | 36 |
| 3. Sodium stearate | 36 |
| 4. Fumed silica | 1.5 |
| 5. Stearic acid | 3.5 |

The ingredients were mixed as described in Example 4 and tablets were prepared using a 9.525 mm die. The hardness and release rates of the 306 mg theophylline tablets were determined as described in the previous examples to give the following results:

| Weight, mg | 383 | | | |
|---|---|---|---|---|
| Thickness, mm | 4.30 | | | |
| Hardness, kg | 4.0 | | | |
|  | Release rate | | | |
| Method | Basket | | Paddle | |
| pH | 1.5 | | 7.0 | |
| Hour | % | Cumulative % | % | Cumulative % |
| 1 | 23.5 | 23.5 | 14.9 | 14.9 |
| 2 | 12.1 | 35.6 | 10.0 | 24.9 |
| 3 | 8.9 | 44.5 | 7.3 | 32.2 |
| 4 | 11.1 | 55.6 | 5.9 | 38.1 |
| 5 | 10.8 | 66.4 | 5.0 | 43.1 |
| 6 | 9.1 | 75.5 | 4.2 | 47.3 |
| 7 | 8.9 | 84.4 | 3.9 | 51.2 |
| 8 | — | — | 3.8 | 55.0 |
| 9 | — | — | 3.4 | 58.4 |
| 10 | — | — | 3.3 | 61.7 |
| 12 | — | — | 5.5 | 67.2 |
| 14 | — | — | 5.4 | 72.6 |
| 16 | — | — | 4.4 | 77.0 |
| 18 | — | — | 4.0 | 81.0 |

EXAMPLES 6–7

Controlled release theophylline tablets were prepared from anhydrous theophylline and 15,000 mPa.sec viscosity grade HPMC having 19–24 weight-% methoxyl content, 4–12 weight-% hydroxypropoxyl content and a number average molecular weight of 124,000, commercially available as Methocel K15M. The tablets were prepared in the presence and in the absence of sodium laurate.

The 306 mg theophylline tablets were prepared from the following ingredients:

|  | Example No. | |
|---|---|---|
|  | 6 | 7 |
| Ingredients | mg/tablet | mg/tablet |
| 1. Theophylline, anhydrous | 306 | 306 |
| 2. HPMC K15M | 18 | 18 |
| 3. Sodium laurate | 0 | 36 |
| 4. Fumed silica | 1.5 | 1.5 |
| 5. Stearic acid | 3.5 | 3.5 |

The ingredients were mixed as described in Examples 1–2 and compressed in a pellet press using a 9.525 mm die.

The release rates were determined at pH 1.5 at 37° C. using the rotating basket method at 100 rpm. The 306 mg theophylline tablets had the following properties:

|  | Example No. | |
|---|---|---|
|  | 6 | 7 |
| Sodium laurate | Absent | Present |
| Weight, mg | 329 | 365 |

-continued

|  | Thickness, mm | 3.70 | 4.30 | |
|---|---|---|---|---|
|  | Hardness, kg | 4.0 | 4.0 | |
| Release rate | | Cumulative | | Cumulative |
| Hour | % | % | % | % |
| 1 | 48.2 | 48.2 | 28.2 | 28.2 |
| 2 | 20.7 | 68.9 | 13.7 | 41.9 |
| 3 | 10.6 | 79.5 | 12.6 | 54.5 |
| 4 | 15.7 | 95.2 | 9.9 | 64.4 |
| 5 | 3.1 | 98.3 | 6.3 | 70.7 |
| 6 | — | — | 5.8 | 76.5 |
| 7 | — | — | 7.6 | 84.1 |

EXAMPLES 8–9

Controlled release ibuprofen tablets were prepared from ibuprofen and the 4000 mPa.sec viscosity grade HPMC (Methocel K4M) used in Examples 1–2. The tablets were prepared in the absence and in the presence of sodium stearate.

The 700 mg ibuprofen tablets were prepared from the following ingredients:

|  |  | Example No. | |
|---|---|---|---|
|  |  | 8 | 9 |
| Ingredients | | mg/tablet | mg/tablet |
| 1. | Ibuprofen | 700 | 700 |
| 2. | HPMC K4M | 90 | 90 |
| 3. | Sodium stearate | 0 | 15.6 |
| 4. | Hydrogenated vegetable oil | 15 | 15.3 |
| 5. | Fumed silica | 6.5 | 6.5 |

The ingredients were mixed as described in Examples 1–2 and compressed in a pellet press using a 9.525 mm die.

The release rates were determined at pH 7.2 at 37° C. using the rotating basket method at 100 rpm. The 700 mg ibuprofen tablets had the following properties:

|  | Example No. | |
|---|---|---|
|  | 8 | 9 |
| Sodium stearate | Absent | Present |
| Weight, mg | 812 | 827 |
| Thickness, mm | 6.0 | 6.1 |
| Hardness, kg | 9.0 | 8.5 |
| Release rate | | Cumulative | | Cumulative |
| Hour | % | % | % | % |
| 1 | 60.9 | 60.9 | 29.0 | 29.0 |
| 2 | 11.8 | 72.7 | 6.4 | 35.4 |
| 3 | 8.3 | 81.0 | 5.6 | 41.0 |
| 4 | 5.0 | 86.0 | 4.9 | 45.9 |
| 5 | 3.2 | 89.2 | 4.3 | 50.2 |
| 6 | 3.0 | 92.2 | 4.5 | 54.7 |
| 7 | 1.5 | 93.7 | 4.2 | 58.9 |
| 8 | 1.3 | 95.0 | 1.6 | 60.7 |
| 9 | 0.7 | 95.7 | 3.3 | 64.0 |
| 10 | 0.3 | 96.0 | 3.5 | 67.5 |

EXAMPLES 10–11

Controlled release aspirin tablets were prepared from U.S.P. aspirin and the 4000 mPa.sec viscosity grade HPMC (Methocel K4M) used in Examples 1–2. The tablets were prepared in the absence and in the presence of sodium stearate.

The 650 mg aspirin tablets were prepared from the following ingredients:

|  |  | Example No. | |
|---|---|---|---|
|  |  | 10 | 11 |
| Ingredients | | mg/tablet | mg/tablet |
| 1. | Aspirin | 650 | 650 |
| 2. | HPMC K4M | 65 | 65 |
| 3. | Sodium stearate | 0 | 30 |
| 4. | Hydrogenated vegetable oil | 7 | 7 |
| 5. | Fumed silica | 0.5 | 0.5 |

The ingredients were mixed as described in Examples 1–2. The mixture was subjected to compression in a tabletting machine having a 7.13×15.88 mm punch under a compression pressure of 27.45 MPa to make 1000 capsule-shaped tablets bisected on one side.

The release rates were determined at a pH 4.5 at 37° C. using the rotating paddle method at 100 rpm., with the following results:

|  | Example No. | |
|---|---|---|
|  | 10 | 11 |
| Sodium stearate | Absent | Present |
| Weight, mg | 722 | 750 |
| Thickness, mm | 6.35 | 6.60 |
| Release rate | | Cumulative | | Cumulative |
| Hour | % | % | % | % |
| 1 | 15.7 | 15.7 | 21.8 | 21.8 |
| 2 | 23.6 | 39.3 | 12.2 | 34.0 |
| 3 | 19.6 | 58.9 | 11.5 | 45.5 |
| 4 | 16.4 | 75.3 | 10.4 | 55.9 |
| 5 | 4.7 | 88.0 | 8.3 | 64.2 |
| 6 | 9.7 | 97.7 | 9.2 | 73.4 |
| 7 | — | — | 8.0 | 81.4 |
| 8 | — | — | 6.6 | 88.0 |

What is claimed is:

1. A therapeutically active solid unit dosage form having a controlled and sustained release pattern upon administration comprising a mixture of a therapeutically active medicament and a carrier base material consisting essentially of (a) one or more water-soluble nonionic cellulose ethers, wherein at least one of the cellulose ethers is a hydroxypropylmethylcellulose having a number average molecular weight of at least 50,000, and (b) an alkali metal carboxylate, wherein the carrier base comprises less than 30 weight-% of the total weight of the dosage form.

2. The composition of claim 1 where the carrier base material contains hydroxypropylmethylcellulose and alkali metal carboxylate in a weight ratio of 1/0.05 to ½.

3. The composition of claim 1 where the alkali metal carboxylate is the salt of a $C_8$ to $C_{40}$ carboxylic acid.

4. The composition of claim 3 wherein the alkali metal carboxylate is sodium stearate or sodium laurate.

5. The composition of claim 2 wherein the hydroxypropylmethylcellulose comprises 3 to 25 weight-% of the total weight of the dosage form.

6. The composition of claim 1 wherein the hydroxypropylmethylcellulose has a methoxyl content of 28–30 weight-% and a hydroxypropoxyl content of 7.5–12 weight-%.

7. The composition of claim 1 wherein the hydroxypropylmethylcellulose has a methoxyl content of 19–24 weight-% and a hydroxypropoxyl content of 4–12 weight-%.

8. A method for the preparation of a therapeutically active unit dosage form having a controlled and sustained release pattern upon administration comprising mixing, shaping and compressing a therapeutically active medicament and a carrier base material consisting essentially of (a) an alkali metal carboxylate, and (b) one or more water-soluble nonionic cellulose ethers, at least one of which is hydroxypropylmethylcellulose having a number average molecular weight of at least 50,000, wherein the carrier base comprises less than 30 weight-% of the total weight of the dosage form.

9. The method of claim 8 wherein the hydroxypropylmethylcellulose constitutes 3 to 25 weight-% of the total weight of the dosage form and the weight ratio of hydroxypropylmethylcellulose to alkali metal carboxylate is in the range of 1/0.05 to ½.

10. The method of claim 9 wherein the alkali metal carboxylate is the salt of a $C_8$ to $C_{40}$ carboxylic acid.

* * * * *